United States Patent
van der Spoel et al.

(10) Patent No.: US 6,537,967 B1
(45) Date of Patent: Mar. 25, 2003

(54) PENTAMER PEPTIDE AMIDE, ALGPGNH$_2$, WHICH INHIBITS VIRAL INFECTIVITY AND METHODS OF USE THEREOF

(75) Inventors: David van der Spoel, Uppsala (SE); Csaba Hetényi, Uppsala (SE); Ákos Végvári, Uppsala (SE); Stefan Höglund, Uppsala (SE); Jin Su, Toronto (CA); Sarah Sandin-Reneby, Stockholm (SE); Laura Goobar-Larsson, Stockholm (SE); Anders Vahlne, Stockholm (SE)

(73) Assignee: Tripep AB, Halsovagen (SE)

( * ) Notice: Subject to any disclaimer, the term of this patent is extended or adjusted under 35 U.S.C. 154(b) by 0 days.

(21) Appl. No.: 10/217,933

(22) Filed: Aug. 12, 2002

Related U.S. Application Data

(63) Continuation of application No. 09/948,372, filed on Sep. 6, 2001, now Pat. No. 6,455,670.

(51) Int. Cl.$^7$ .............................................. A61K 38/04
(52) U.S. Cl. ............................. 514/2; 514/18; 530/300; 530/331
(58) Field of Search ....................... 514/2, 18; 530/300, 530/331

(56) References Cited

U.S. PATENT DOCUMENTS 6,258,932 B1 * 7/2001 Vahlne ....................... 530/331

FOREIGN PATENT DOCUMENTS

| EP | 0 421 074 A1 | | 4/1991 |
|---|---|---|---|
| EP | 0 900 566 A1 | | 3/1999 |
| WO | WO 89/02277 | * | 3/1989 |
| WO | WO 90/04390 | | 5/1990 |
| WO | WO 99/09056 | | 2/1999 |
| WO | WO 01/10456 | | 2/2001 |
| WO | WO 01/10457 | | 2/2001 |

OTHER PUBLICATIONS

Ashkenazi et al., "Safety and antitumor activity of recombinant soluble Apo2 ligand," *J Clinical Investigation*, 104(2):155–162 (1999).

Van Der Spoel et al., "Tripeptide Amides that Block Viral Infectivity and Methods of use Thereof," U.S. patent application Ser. No. 09/938,806, filed Aug. 24, 2001.

Vahlne, "Protein Polymerization Inhibitors and Methods of Use," U.S. patent application Ser. No. 10/072,783, filed Feb. 8, 2002.

Goobar–Larsson et al., "Molecules that Block Viral Infectivity and Methods of Use Thereof," U.S. patent application, filed Sep. 3, 2002.

* cited by examiner

*Primary Examiner*—Jeffrey Stucker
(74) *Attorney, Agent, or Firm*—Knobbe, Martens, Olson & Bear

(57) ABSTRACT

The present invention relates to the discovery that a specific pentamer peptide amide, which corresponds to a viral capsid sequence, can be used to inhibit viral infection, including human immunodeficiency virus (HIV) infection. More specifically, medicaments comprising said pentamer peptide amide and methods of using said compounds for the prevention and treatment of viral infection, such as HIV infection, are provided.

8 Claims, 2 Drawing Sheets

PENTAMER PEPTIDE AMIDE, ALGPGNH$_2$, WHICH INHIBITS VIRAL INFECTIVITY AND METHODS OF USE THEREOF

RELATED APPLICATION

This application is a Continuation of U.S. application Ser. No. 09/948372, filed Sep. 6, 2001, now U.S. Pat. No. 6,455,670, which is hereby expressly incorporated by reference in its entirety.

FIELD OF THE INVENTION

The present invention relates to the discovery that a specific pentamer peptide amide, which corresponds to a viral capsid sequence, can be used to inhibit viral infection, including human immunodeficiency virus (HIV) infection. More specifically, medicaments comprising said pentamer peptide amide and methods of using said compounds for the prevention and treatment of viral infection, such as HIV infection, are provided.

BACKGROUND OF THE INVENTION

All viruses are composed of a protein shell surrounding a nucleic acid containing core. The protein shell directly surrounding the viral nucleic acid is called a capsid, whereas, the complete protein-nucleic acid complex having both the capsid and the nucleic acid is called a nucleocapsid. Arenaviruses, rotaviruses, orbiviruses, retroviruses (including lentiviruses), papillomaviruses, adenoviruses, herpesviruses, paramyxovirus, myxovirus, and hepadnaviruses all exhibit these general structural features. (*Virology,* Fields ed., third edition, Lippencott-Raven publishers, pp 1513, 1645,1778, 2047, 2113, 2221, and 2717 (1996)).

The capsid is composed of many subunits (capsomeres) and capsomeres are formed from several homo- or hetero-polymers of protein. The noncovalent bonds between capsomeres in a viral assembly are of the same sort that stabilize a folded protein domain. The interface between two subunits can look very much like a single domain, with amino acid side chains tightly packed against one another. A common feature to most of the virus structures analyzed is the way in which a polypeptide chain from one capsomere can extend under or over domains of neighboring capsomeres. These extended polypeptide arms intertwine with other polypeptide arms and help to stabilize the capsid by initiating hydrophobic interactions, hydrogen bonding, and salt bridges. Contacts between individual capsomeres, and for some viruses also contacts with core proteins, determine the overall capsid structure and if a number of identical capsomeres are involved, repeated contacts occur and the resulting structure is symmetrical. (Id. at 62).

Some simple viruses form spontaneously from their dissociated components while others require enzyme-catalyzed modifications of the capsomeres to trigger assembly. Viral self assembly is driven by the stability of the interactions between protein subunits under conditions that favor association. More complex viruses are often constructed from subassemblies that have undergone self assembly processes. (Id. at pp 62, 70, 1646 and 1888). Although the capsids of many viruses differ in protein composition, a general viral structural design has evolved characterized by polymerized capsomeres that, in turn, are composed of several homo- or hetero-polymers of protein.

HIV is the name given to a lentivirus that infects humans and that causes acquired immuno-deficiency syndrome (AIDS). The lentivirus isolates from humans are grouped into one of two types (HIV-1 and HIV-2) on the basis of serologic properties and sequence analysis of molecularly cloned viral genomes. Genetically distinct lentiviruses have been obtained from several non-human primate species including African green monkeys, sooty magabeys, mandrills, chimpanzees, and sykes. Collectively, the lentivirus isolates from non-human primates are called SIV. Sequence analysis reveals that the genomes of some SIV strains and HIV-1 and HIV-2 strains exhibit a high degree of homology. Further, electron microscopy reveals that the ultrastructure of HIV and SIV are similar in that both have virions about 110 nm in diameter with a cone-shaped nucleocapsid surrounded by a lipid bilayer membrane that contains envelope glycoprotein spikes. (Id. at pp. 1882–1883).

HIV is a complex retrovirus containing at least seven genes. The viral structural genes, designated gag, pol, and env, respectively code for the viral core proteins, reverse transcriptase, and the viral glycoproteins of the viral envelope. The remaining HIV genes are accessory genes involved in viral replication. The gag and env genes encode polyproteins, i.e., the proteins synthesized from each of these genes are post-translationally cleaved into several smaller proteins.

Although the overall shape of HIV and SIV virions is spherical, the nucleocapsid is asymmetrical having a long dimension of about 100 nm, a wide free end about 40–60 nm, and a narrow end about 20 nm in width. The nucleocapsid within each mature virion is composed of two molecules of the viral single-stranded RNA genome encapsulated by proteins proteolytically processed from the Gag precursor polypeptide. Cleavage of the gag gene polyprotein Pr55$_{gag}$ by a viral coded protease (PR) produces mature capsid proteins. These gag gene products are the matrix protein (p17), that is thought to be located between the nucleocapsid and the virion envelope; the major capsid protein (p24), that forms the capsid shell; and the nucleocapsid protein (p9), that binds to the viral RNA genome. This proteolytic processing in infected cells is linked to virion morphogenesis. (Id. at pp 1886–1887).

The major capsid protein p24 (also called CA) contains about 240 amino acids and exhibits a molecular weight of 24–27 kD. The protein p24 self-associates to for mn dimers and oligomeric. complexes as large as dodecamers. Genetic studies with mutations in the HIV-1 gag polyprotein have identified several functional domains in the p24 protein including the C terminal half of the molecule and a major homology region (MHR) spanning 20 amino acids that is conserved in the p24 proteins of diverse retroviruses. These mutations appear to affect precursor nucleocapsid assembly. (Id. at pp 1888–1889).

Since the discovery of HIV-1 as the etiologic agent of AIDS, significant progress has been made in understanding the mechanisms by which the virus causes disease. While many diagnostic tests have been developed, progress in HIV vaccine therapy has been slow largely due to the heterogeneous nature of the virus and the lack of suitable animal models. (See, e.g., Martin, *Nature,* 345:572–573 (1990)).

A variety of pharmaceutical agents have been used in attempts to treat AIDS. Many, if not all, of these drugs, however, create serious side effects that greatly limit their usefulness as therapeutic agents. HIV reverse transcriptase is one drug target because of its crucial role in viral replication. Several nucleoside derivatives have been found to inhibit HIV reverse transcriptase including azidothymidine (AZT, zidovidine®). AZT causes serious side effects such that many patients cannot tolerate its administration. Other nucleoside analogs that inhibit HIV reverse transcriptase have been found to cause worse side effects than AZT. Another drug target is the HIV protease (PR) crucial to virus development. PR is an aspartic protease and can be inhibited by synthetic compounds. (Richards, *FEBS Lett.*, 253:214–216 (1989)). Protease inhibitors inhibit the growth of HIV more effectively than reverse transcriptase inhibitors but prolonged therapy has been associated with metabolic diseases such as lipodystrophy, hyperlipidemia, and insulin resistance.

Additionally, HIV quickly develops resistance to nucleoside/nucleotide analogue reverse transcriptase inhibitors and protease inhibitors. This resistance can also spread between patients. Studies have shown, for example, that one tenth of the individuals recently infected by HIV already have developed resistance to AZT, probably because they were infected by a person that at the time of transmission carried a virus that was resistant to AZT.

It would be useful in the treatment and prevention of viral infections, including HIV and SIV, to have specific and selective therapeutic agents that cause few, if any, side effects.

SUMMARY OF THE INVENTION

The present invention relates to the discovery that a pentamer peptide amide ALGPG-$NH_2$ (SEQ. ID. NO.: 1) inhibits viral infectivity, specifically HIV. An intact capsid structure is of vital importance for the infectivity of a virion. A way to disrupt assembly of capsid protein macromolecules, that for their infectivity are dependent on di-, tri-, tetra-, or poly-merization, is to construct small molecules that affect such protein-protein interactions. It is contemplated that the pentamer peptide amide ALGPG-$NH_2$ (SEQ. ID. NO.: 1) inhibits viral infectivity by disrupting the proper assembly of the viral capsid. Thus, aspects of the present invention relate to the pentamer peptide amide ALGPG-$NH_2$ (SEQ. ID. NO.: 1) and its ability to disrupt viral capsid assembly.

It is believed that ALGPG-$NH_2$ (SEQ. ID. NO.: 1) binds to a protein that is involved in capsomere organization and capsid assembly of HIV-1, HIV-2, and SIV and thereby inhibits and/or prevents proper capsid assembly and, thus, viral infection. This pentamer peptide amide and peptidomimetics resembling its structure (collectively referred to as "peptide agents") are used in a monomeric or multimeric form. These peptide agents are suitable for therapeutic and prophylactic application in mammals, including man, suffering from viral infection, specifically HIV infection.

In one embodiment, a composition for inhibiting viral replication in host cells infected with a virus comprises an effective amount of a peptide amide that comprises, consists of, or consists essentially of ALGPG-$NH_2$ (SEQ. ID. NO.: 1). In some embodiments, the compositions described above are joined to a support and in other embodiments, the compositions described above are incorporated into a pharmaceutical having a pharmaceutically acceptable carrier.

Methods of inhibiting viral replication in a host cell are also embodiments of the present invention. One approach, for example, involves administering to a cell an effective amount of a peptide amide comprising, consisting of, or consisting essentially of ALGPG-$NH_2$ (SEQ. ID. NO.: 1). The method described above can be supplemented with an antiviral treatment selected from the group consisting of nucleoside analogue reverse transcriptase inhibitors, nucleotide analogue reverse transcriptase inhibitors, non-nucleoside reverse transcriptase inhibitors, and protease inhibitors. The ALGPG-NH2 (SEQ. ID. NO.: 1) used in the method above can be joined to a support or can be administered in a pharmaceutical comprising a pharmaceutically acceptable carrier.

In another embodiment, a composition for inhibiting HIV replication in host cells comprises an effective amount of a peptide amide that comprises, consists of, or consists essentially of ALGPG-$NH_2$ (SEQ. ID. NO.: 1). In some embodiments, the ALGPG-$NH_2$ (SEQ. ID. NO.: 1) is joined to a support and in other embodiments, it is incorporated into a pharmaceutical comprising a pharmaceutically acceptable carrier.

In another method, an approach to inhibit HIV replication in host cells is provided, which involves administering to said cells a peptide amide that comprises, consists of, or consists essentially of an effective amount of ALGPG-$NH_2$ (SEQ. ID. NO.: 1). This method can also be supplemented by an antiviral treatment selected from the group consisting of nucleoside analogue reverse transcriptase inhibitors, nucleotide analogue reverse transcriptase inhibitors, non-nucleoside reverse transcriptase inhibitors, and protease inhibitors. Further, the ALGPG-$NH_2$ (SEQ. ID. NO.: 1) used in this method can be Joined to a support or can be administered in a pharmaceutical comprising a pharmaceutically acceptable carrier.

In another method, an approach for interrupting viral capsid assembly is provided. This approach involves contacting a cell with an effective amount of a peptide amide that comprises, consists of, or consists essentially of an effective amount of ALGPG-$NH_2$ (SEQ. ID. NO.: 1). The pentamer peptide amide ALGPG-$NH_2$ (SEQ. ID. NO.: 1) used in this method can also be joined to a support or incorporated in a pharmaceutical.

In still another method, an approach for interrupting HIV capsid assembly is provided. This approach also involves contacting a cell with an effective amount of a peptide amide that comprises, consists of, or consists essentially of an effective amount of ALGPG-$NH_2$ (SEQ. ID. NO.: 1). The pentamer peptide amide ALGPG-$NH_2$ (SEQ. ID. NO.: 1) used in this method can also be joined to a support or incorporated in a pharmaceutical.

Methods of making antiviral pharmaceuticals are also embodiments of the invention. By one approach, a peptide amide that comprises, consists of, or consists essentially of an effective amount of ALGPG-$NH_2$ (SEQ. ID. NO.: 1) is provided and then said peptide amide is mixed with a pharmaceutically acceptable carrier or is otherwise formulated for human use. Preferred antiviral pharmaceuticals are formulated for oral administration, however, many other routes of administration are contemplated. The antiviral pharmaceutical embodied herein can also include known antiviral compounds, for example, nucleoside analogue reverse transcriptase inhibitors, nucleotide analogue reverse transcriptase inhibitors, non-nucleoside reverse transcriptase inhibitors, and protease inhibitors incorporated into the pharmaceutical.

DETAILED DESCRIPTION OF THE PREFERRED EMBODIMENT

Figure 1:
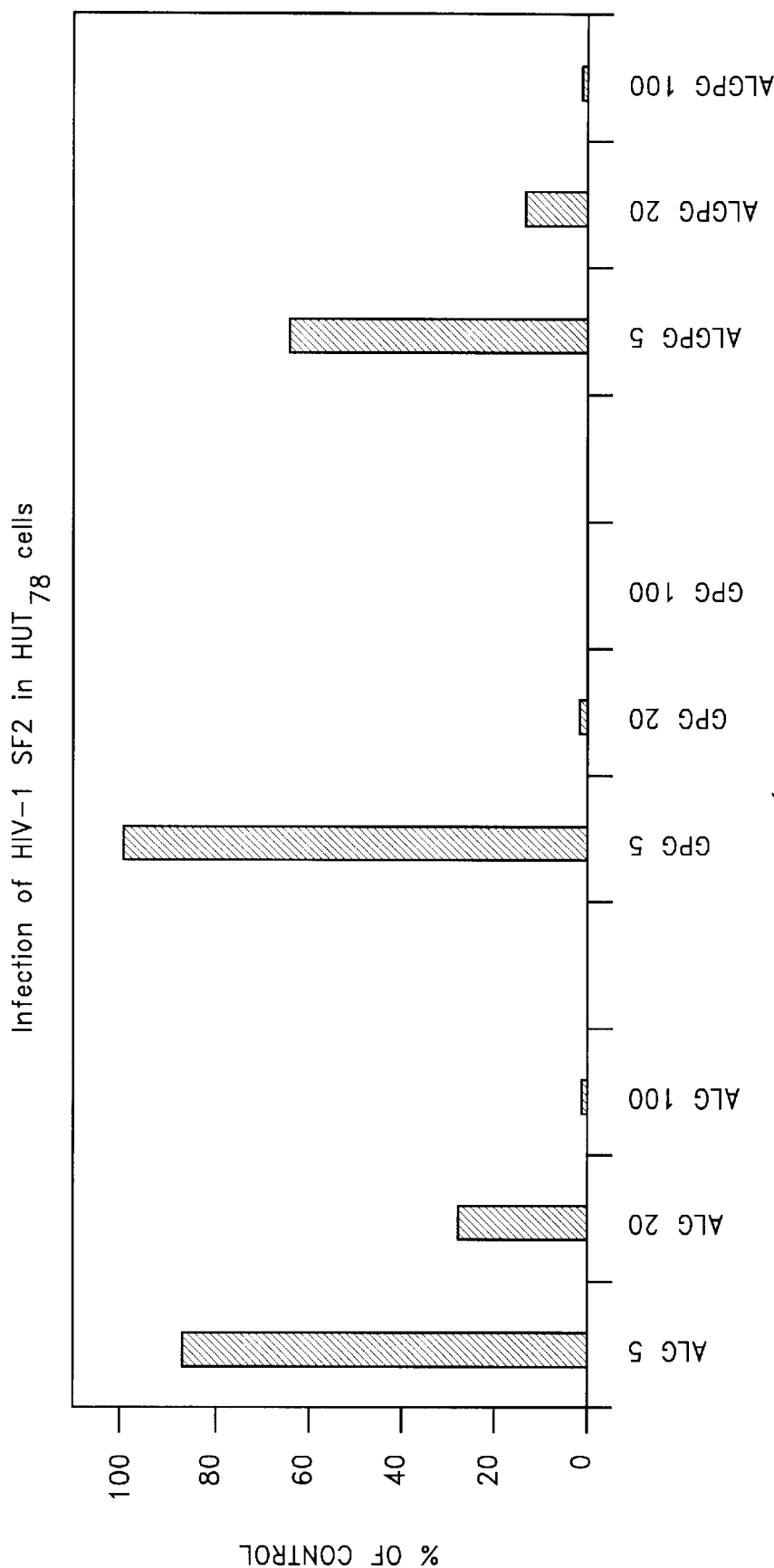
FIG. 1 shows the antiviral activity of ALGPG-$NH_2$ (SEQ. ID. NO.: 1) as compared to ALG-$NH_2$ and GPG-$NH_2$ in H9 cells infected with HIV-1SF2 obtained from $HUT_{78}$ cells.

It has been discovered that a pentamer peptide amide with a sequence that corresponds to viral capsid proteins prevents and/or inhibits viral infection by interrupting proper nucleocapsid formation. This pentamer peptide amide is useful in the treatment of viral disease, particularly in HIV/AIDS afflicted subjects, and as preventive agents for patients at-risk of viral infection, particularly HIV infection, and for use with medical devices where the risk of exposure to virus is significant.

The disclosure below demonstrates that a peptide amide that comprises, consists of, or consists essentially of an effective amount of ALGPG-$NH_2$ (SEQ. ID. NO.: 1) inhibits the replication of viruses, such as HIV-1. Although it was generally known that small peptide amides can be used to inhibit HIV infection, the anti HIV activity of ALGPG-$NH_2$ (SEQ. ID. NO.: 1) has not been previously recognized. (See e.g., U.S. Pat. Nos. 5,627,035 and 6,258,932 to Vahlne, which are both herein expressly incorporated by reference in their entireties). Evidence of the ability of ALGPG-$NH_2$ (SEQ. ID. NO.: 1) to inhibit HIV replication was found in viral infectivity assays that monitored the amount of capsid protein or reverse transcriptase activity present in culture supernatant.

Several approaches to making biotechnological tools and pharmaceutical compositions comprising ALGPG-$NH_2$ (SEQ. ID. NO.: 1) and peptidomimetics that resemble this pentamer peptide amide (collectively referred to as "peptide agents") are given below. In some embodiments, the peptide agents are provided in monomeric form; in others, the peptide agents are provided in multimeric form or in multimerized form. Support-bound peptide agents are also used in several embodiments.

Pharmaceutical compositions comprising peptide agents are administered as therapeutics or prophylactics or both for the treatment and/or prevention of viral disease, particularly, HIV infection. In some embodiments, the pharmaceutical compositions comprising peptide agents are either formulated with or administered in combination with other antiviral treatments including nucleoside analogue reverse transcriptase inhibitors, nucleotide analogue reverse transcriptase inhibitors, non-nucleoside reverse transcriptase inhibitors, and protease inhibitors. EXAMPLE 1 describes how the ALGPG-$NH_2$ (SEQ. ID. NO.: 1) used in the experiments disclosed herein was obtained and other approaches, which can be used to obtain this antiviral therapeutic.

EXAMPLE 1

The peptides GPG-NH2, ALG-NH2, and ALGPG-NH2 used in the experiments described herein were obtained by custom order from Bachem Feinchemikalien AG (Bubendorf, Switzerland). These molecules can also be synthesized according to the approaches described in Horal et al., *Proc. Natl. Acad. Sci. USA* 88:5754–8 (1991). The peptide amides, for example, can be chemically synthesized with an automated peptide synthesizer (Syro, Multisyntech, Tubingen, Germany) using 9-fluorenylmethoxycarbonyl (fmoc) protected amino acids (Milligen, Bedford, Mass.) according to standard protocols. All peptides are preferably lyophilized and then dissolved at the appropriate concentration in phosphate-buffered saline (PBS). The peptides are also preferably analyzed by reverse phase high performance liquid chromatography (RP-HPLC) using a PepS-15 C18 column (Pharmacia, Uppsala, Sweden), prior to use.

The amide modification is created by substituting an amino group for the hydroxyl residue normally present at the terminal carboxyl group of a peptide. That is, instead of a terminal COOH, the peptides are synthesized to have CO-$NH_2$. The disclosure below describes the assays that were used to verify that ALGPG-$NH_2$ (SEQ. ID. NO.: 1) inhibits HIV-1 infection.

ALGPG-$NH_2$ (SEQ. ID. NO.: 1) inhibits and/or prevents HIV replication and infection The pentamer peptide amide ALGPG-$NH_2$ (SEQ. ID. NO.: 1), which corresponds to residues 204 to 208 of the capsid protein p24, was thought to effect capsid assembly of the HIV virus and thereby inhibit HIV replication. To verify this hypothesis, the pentamer amide ALGPG-$NH_2$ (SEQ. ID. NO.: 1) was obtained according to EXAMPLE 1 and was tested in several HIV-1 infectivity assays. The efficiency of HIV-1 replication and the status of HIV-1 infection was monitored by reverse transcriptase activity and the concentration of p24 protein in the cell supernatant. (See e.g., U.S. Pat. Nos. 5,627,035 and 6,258,932, which describe similar HIV infectivity assays and others that can be used to analyze ALGPG-$NH_2$ (SEQ. ID. NO.: 1)). EXAMPLE 2 describes these experiments in greater detail.

EXAMPLE 2

In this example, the methods that were used to analyze the ability of ALGPG-$NH_2$ (SEQ. ID. NO.: 1) to inhibit HIV-1 replication are disclosed. HIV-1 SF-2 stock was prepared from $HUT_{78}$ cells and two clinical isolates were prepared from donor's peripheral blood mononuclear cells (PBMC). The virus infected cells were propagated and maintained in RPMI 1640 medium supplemented with 10% heat inactivated fetal bovine serum (GIBCO Laboratories) with penicillin and streptomycin (100 $\mu$g/ml each). PBMCs were purified by Ficoll-Hypaque density gradient centrifugation and stimulated with phytohemagglutinin (KEBO laboratories, Sweden) for three days in RPMI 1640 medium supplemented with 10% heat inactivated fetal bovine serum (GIBCO Laboratories) with penicillin and streptomycin (100 $\mu$g/ml each).

Approximately $10^5$ of H9 cells were infected with HIV-1 SF-2, obtained as described above, at 25 $TCID_{50}$ to test the inhibitory effect of ALGPG-$NH_2$ (SEQ. ID. NO.: 1). The H9 cells were resuspended with or without ALGPG-$NH_2$ (SEQ. ID. NO.: 1) (at approximately 5 $\mu$M, 20 $\mu$M, and 100:M) in 1 ml of RPMI 1640 medium supplemented with 10% (v/v) heat-inactivated fetal bovine serum (FBS), penicillin (100 $\mu$/ml), and streptomycin (100 u/ml), all available through GIBCO, and Polybrene (2 $\mu$g/ml), available through Sigma. Thereafter, viruses were added at 25 $TCID_{50}$ in a volume of 20–30 $\mu$l. Cells were incubated with virus at 37° C. for 1 hr then pelleted at 170×g for 7 minutes. The cells were then washed three times in RPMI medium with or without peptides at room temperature and pelleted at 170×g for 7 minutes, as above. After the final wash, the cells were resuspended in RPMI culture medium containing the peptides in a 24-well plate (Costar corporation) and were kept at 37° C. in 5% $CO_2$ with humidity.

Culture supernatants were collected and analyzed when the medium was changed at 4, 7, 10, and 14 days post infection. To monitor the replication of virus, reverse transcriptase (RT) activity in the supernatants was assayed using a commercially available Lenti-RT activity kit. (Cavidi Tech, Uppsala, Sweden). The amount of RT was determined with the aid of a regression line of standards. The presence of p24 in the supernatants was determined using a commercially available HIV p24 antigen detection kit (ELISA kit from Abbott Laboratories, North Chicago, U.S.A.). The results from this data were compiled and are provided in FIG. 1.

As shown in FIG. 1, as little as 5 μM ALGPG-NH$_2$ (SEQ. ID. NO.: 1) effectively inhibited HIV-1 SF-2 infection in H9 cells. Significantly, ALGPG-NH$_2$ (SEQ. ID. NO.: 1) was more effective than GPG-NH$_2$ at the 5 μM concentration (an approximately 50% inhibition was obtained with ALGPG-NH$_2$ (SEQ. ID. NO.: 1), whereas, an approximately 15% inhibition was obtained with ALG-NH$_2$ and 10% inhibition was obtained with GPG-NH$_2$). When concentrations of peptide amides were raised to 20 μM or 100 μM, inhibition by ALGPG-NH$_2$ (SEQ. ID. NO.: 1) was almost complete.

The infectivity assays of the HIV-1 clinical isolates were performed, as above, in PBMC, which were stimulated for three days with 2.5 μg/ml of phytohemagglutinin (DIFCO, New Jersey). Cells were cultured in RPMI 1640 medium supplemented with 10% (v/v) heat-inactivated fetal bovine serum (FBS), penicillin (100 u/ml), and streptomycin (100 u/ml), all available through GIBCO, and Polybrene (2 μg/ml), available through Sigma. Approximately 25TCID$_{50}$/2×10$^5$ cells were incubated with or without GPG-NH$_2$, ALG-NH$_2$, or ALGPG-NH$_2$ (SEQ. ID. NO.: 1) at 20 μM or 100 μM concentrations. The production of p24 in the culture supernatent was monitored using a commercially available HIV p24 antigen detection kit (ELISA kit from Abbott Laboratories, North Chicago, U.S.A.). The results from this data were compiled and are provided in FIG. 2.

Figure 2:
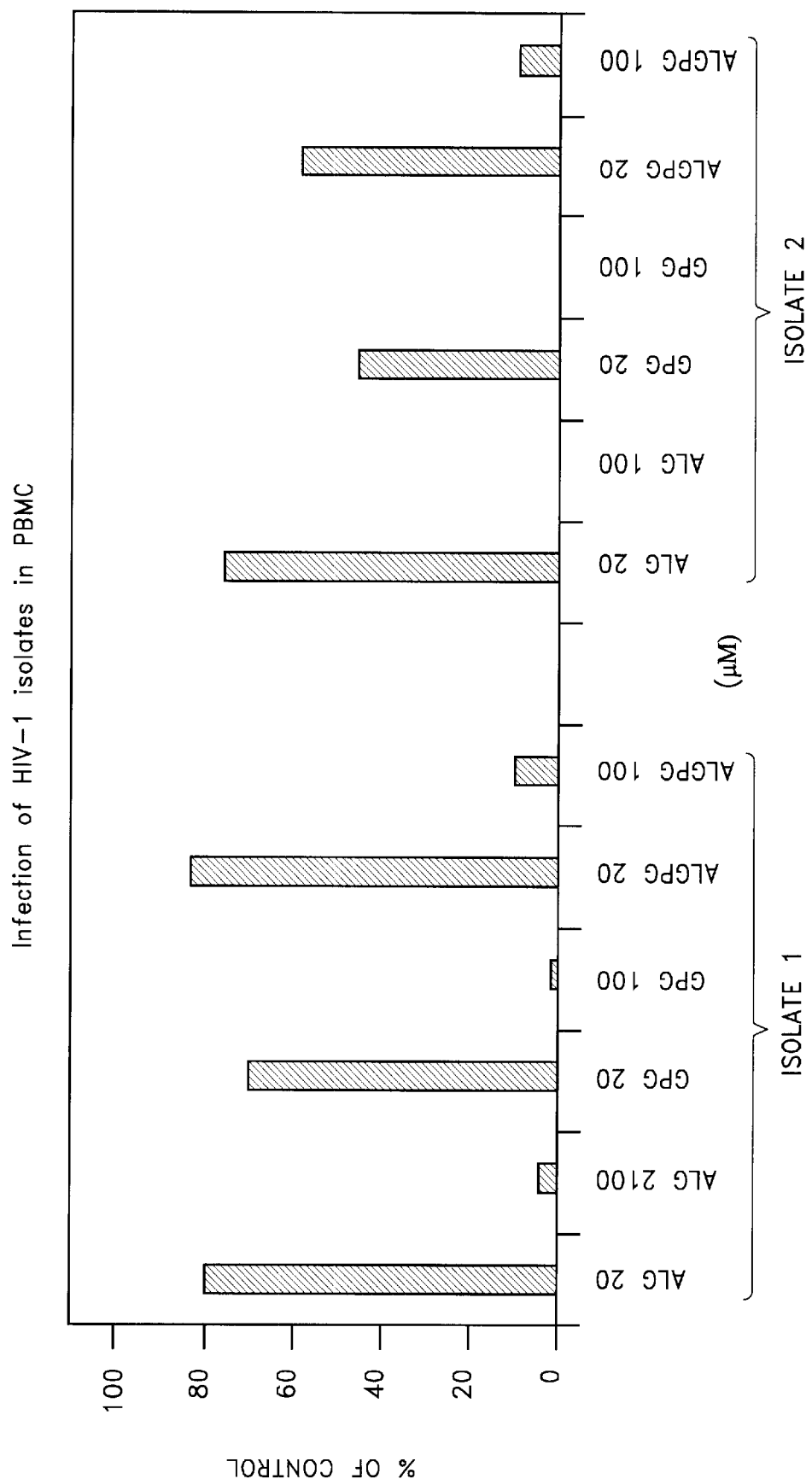
FIG. 2 shows the antiviral activity of ALGPG-$NH_2$ (SEQ. ID. NO.: 1) as compared to ALG-$NH_2$ and GPG-$NH_2$ in H9 cells infected with two clinical isolates of HIV obtained from peripheral blood mononuclear cells (PBMC).

As shown in FIG. 2, 20 μM ALGPG-NH$_2$ (SEQ. ID. NO.: 1) provided approximately 20% inhibition of isolate 1 and approximately 50% inhibition of isolate 2, whereas, 100 μM ALGPG-NH$_2$ (SEQ. ID. NO.: 1) provided almost complete inhibition of both isolates. The results provided in this example demonstrate that ALGPG-NH$_2$ (SEQ. ID. NO.: 1) effectively inhibits the infectivity or replication of HIV. In the following section, several approaches are provided to make biotechnological tools and pharmaceutical compositions comprising ALGPG-NH$_2$ (SEQ. ID. NO.: 1).

Biotechnological tools and pharmaceutical compositions comprising ALGPG-NH$_2$ (SEQ. ID. NO.: 1)

Desirable biotechnological tools or components to prophylactic or therapeutic agents provide ALGPG-NH$_2$ (SEQ. ID. NO.: 1) in such a form or in such a way that a sufficient affinity for inhibition of a virus, such as HIV-1, HIV-2, or SIV, is obtained. While a natural monomeric peptide agent (e.g., appearing as discrete units of the peptide agent each carrying only one binding epitope) is sufficient to bind a capsomere protein, such as p24, and/or interfere with capsid assembly and/or prevent viral infection, such as HIV-1, HIV-2, or SIV infection, synthetic ligands or multimeric ligands (e.g., appearing as multiple units of the peptide agent with several binding epitopes) may have far greater ability to bind a capsomere protein, such as p24, and/or interfere with capsid assembly and/or prevent viral infection, such as HIV-1, HIV-2, or SIV infection. It should be noted that the term "multimeric" refers to the presence of more than one unit of a ligand, for example several individual molecules of ALGPG-NH$_2$ (SEQ. ID. NO.: 1), as distinguished from the term "multimerized" that refers to the presence of more than one molecule of ALGPG-NH$_2$ (SEQ. ID. NO.: 1) joined as a single discrete unit in tandem.

A multimeric agent (synthetic or natural) that binds a capsomere protein, such as p24, and/or interferes with capsid assembly and/or inhibits viral infection, such as HIV-1, HIV-2, or SIV infection, may be obtained by coupling ALGPG-NH$_2$ (SEQ. ID. NO.: 1) to a macromolecular support. The term "support" as used herein includes a carrier, a resin or any macromolecular structure used to attach, immobilize, or stabilize a peptide agent. Solid supports include, but are not limited to, the walls of wells of a reaction tray, test tubes, polystyrene beads, magnetic beads, nitrocellulose strips, membranes, microparticles such as latex particles, sheep (or other animal) red blood cells, artificial cells and others. The term "support" also includes carriers as that term is understood for the preparation of pharmaceuticals.

The macromolecular support can have a hydrophobic surface that interacts with a portion of the peptide agent by hydrophobic non-covalent interaction. The hydrophobic surface of the support can also be a polymer such as plastic or any other polymer in which hydrophobic groups have been linked such as polystyrene, polyethylene or polyvinyl. Alternatively, the peptide agent can be covalently bound to carriers including proteins and oligo/polysaccarides (e.g. cellulose, starch, glycogen, chitosane or aminated sepharose). In these later embodiments, a reactive group on the peptide agent, such as a hydroxy or an amino group, can be used to join to a reactive group on the carrier so as to create the covalent bond. The support can also have a charged surface that interacts with the peptide agent. Additionally, the support can have other reactive groups that can be chemically activated so as to attach a peptide agent. For example, cyanogen bromide activated matrices, epoxy activated matrices, thio and thiopropyl gels, nitrophenyl chloroformate and N-hydroxy succinimide chlorformate linkages, and oxirane acrylic supports are common in the art.

The support can also comprise an inorganic carrier such as silicon oxide material (e.g. silica gel, zeolite, diatomaceous earth or aminated glass) to which the peptide agent is covalently linked through a hydroxy, carboxy or amino group and a reactive group on the carrier. Furthermore, in some embodiments, a liposome or lipid bilayer (natural or synthetic) is contemplated as a support and peptide agents are attached to the membrane surface or are incorporated into the membrane by techniques in liposome engineering. By one approach, liposome multimeric supports comprise a peptide agent that is exposed on the surface of the bilayer and a second domain that anchors the peptide agent to the lipid bilayer. The anchor can be constructed of hydrophobic amino acid residues, resembling known transmembrane domains, or can comprise ceramides that are attached to the first domain by conventional techniques.

Supports or carriers for use in the body, (i.e. for prophylactic or therapeutic applications) are desirably physiological, non-toxic and preferably, non-immunoresponsive. Contemplated carriers for use in the body include poly-L-lysine, poly-D, L-alanine, liposomes, and Chromosorb® (Johns-Manville Products, Denver Co.). Ligand conjugated Chromosorb® (Synsorb-Pk) has been tested in humans for the prevention of hemolytic-uremic syndrome and was reported as not presenting adverse reactions. (Armstrong et al. *J. Infectious Diseases*, 171:1042–1045 (1995)). For some embodiments, the administration of a "naked" carrier (i.e., lacking an attached peptide agent) that has the capacity to attach a peptide agent in the body of a subject is contemplated. By this approach, a "prodrug-type" therapy is envisioned in which the naked carrier is administered separately from the peptide agent and, once both are in the body of the subject, the carrier and the peptide agent are assembled into a multimeric complex.

The insertion of linkers, such as λ linkers, of an appropriate length between the peptide agent and the support are also contemplated so as to encourage greater flexibility of the peptide agent and thereby overcome any steric hindrance that may be presented by the support. The determination of an appropriate length of linker that allows for optimal binding to a capsomere protein, such as p24, and/or interference with capsid assembly and/or inhibition of viral infection, such as HIV or SIV infection, can be determined by screening the peptide agents with varying linkers in the assays detailed in the present disclosure.

Another aspect of the invention includes a composite support comprising more than one type of peptide agent. A "composite support" may be a carrier, a resin, or any macromolecular structure used to attach or immobilize two or more different peptide agents that bind to a capsomere protein, such as p24, and/or interfere with capsid assembly and/or inhibit viral infection, such as HIV or SIV infection. In some embodiments, a liposome or lipid bilayer (natural or synthetic) is contemplated for use in constructing a composite support and peptide agents are attached to the membrane surface or are incorporated into the membrane using techniques in liposome engineering. The insertion of linkers, such as 8 linkers, of an appropriate length between the peptide agent and the composite support is also contemplated, as described above.

In other embodiments, the multimeric and composite supports discussed above can have attached multimerized ligands so as to create a "multimerized-multimeric support" and a "multimerized-composite support", respectively. A multimerized ligand can, for example, be obtained by coupling two or more peptide agents in tandem using conventional techniques in molecular biology. The multimerized form of the ligand can be advantageous for many applications because of the ability to obtain an agent with a better ability to bind to a capsomere protein, such as p24, and/or interfere with capsid assembly and/or inhibit viral infection, such as HIV or SIV infection. Further, the incorporation of linkers or spacers, such as flexible 8 linkers, between the individual domains that make-up the multimerized agent is another embodiment. The insertion of 8 linkers of an appropriate length between protein binding domains, for example, can encourage greater flexibility in the molecule and can overcome steric hindrance. Similarly, the insertion of linkers between the multimerized ligand and the support can encourage greater flexibility and limit steric hindrance presented by the support. The determination of an appropriate length of linker that allows for optimal binding to p24 and/or interference with capsid assembly and/or inhibition of HIV or SIV infection, can be determined by screening the ligands with varying linkers in the assays detailed in this disclosure.

In preferred embodiments, the various types of supports discussed above are created using ALGPG-NH$_2$ (SEQ. ID. NO.: 1). The multimeric supports, composite supports, multimerized-multimeric supports, or multimerized-composite supports, collectively referred to as "support-bound agents", are also preferably constructed using ALGPG-$NH_2$ (SEQ. ID. NO.: 1).

The monomeric and multimeric peptide agents described herein are suitable for use as a biotechnological tool to study the interaction of ALGPG-$NH_2$ (SEQ. ID. NO.: 1) with capsid proteins and also as medicaments for the treatment of subjects already infected with a virus, such as HIV or SIV, or as a preventive measure to avoid viral infections, such as HIV or SIV infection. Although anyone could be treated with ALGPG-$NH_2$ (SEQ. ID. NO.: 1) as a prophylactic, the most suitable subjects are people at risk for viral infection. Such subjects include, but are not limited to, the elderly, the chronically ill, homosexuals, prostitutes, intravenous drug users, hemophiliacs, children, and those in the medical profession who have contact with patients or biological samples. The following section discusses methods of making and using the medicaments described herein.

Methods of making and using medicaments comprising ALGPG-$NH_2$ (SEQ. ID. NO.: 1)

Methods of making and using medicaments comprising, consisting of, or consisting essentially of ALGPG-$NH_2$ (SEQ. ID. NO.: 1) are also embodiments of the present invention. The embodiments described herein can be processed in accordance with conventional methods of galenic pharmacy to produce medicinal agents for administration to patients, e.g., mammals including humans. The peptide agents can be incorporated into a pharmaceutical product with and without modification. Further, the manufacture of pharmaceuticals or therapeutic agents that deliver the peptide agent by several routes is included within the scope of the present invention.

The compounds described herein can be employed in admixture with conventional excipients, i.e., pharmaceutically acceptable organic or inorganic carrier substances suitable for parenteral, enteral (e.g., oral) or topical application that do not deleteriously react with the peptide agents. Suitable pharmaceutically acceptable carriers include, but are not limited to, water, salt solutions, alcohols, gum arabic, vegetable oils, benzyl alcohols, polyethylene glycols, gelatine, carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like that do not deleteriously react with the active compounds.

In some embodiments, medicaments comprising peptide agents are formulated with or administered in conjunction with other agents that inhibit viral infections, such as HIV infection, so as to achieve a better viral response. At present four different classes of drugs are in clinical use in the antiviral treatment of HIV-1 infection in humans. These are (i) nucleoside analogue reverse transcriptase inhibitors (NRTIs), such as zidovidine, lamivudine, stavudine, didanosine, abacavir, and zalcitabine; (ii) nucleotide analogue reverse transcriptase inhibitors, such as adetovir and pivaxir; (iii) non-nucleoside reverse transcriptase inhibitors (NNRTIs), such as efavirenz, nevirapine, and delavirdine; and (iv) protease inhibitors, such as indinavir, nelfinavir, ritonavir, saquinavir and amprenavir. By simultaneously using two, three, or four different classes of drugs in conjunction with administration of the peptide agents, HIV is less likely to develop resistance, since it is less probable that multiple mutations that overcome the different classes of drugs and the peptide agents will appear in the same virus particle.

It is thus preferred that medicaments comprising peptide agents be formulated with or given in combination with nucleoside analogue reverse transcriptase inhibitors, nucleotide analogue reverse transcriptase inhibitors, non-nucleoside reverse transcriptase inhibitors, and protease inhibitors at doses and by methods known to those of skill in the art. Medicaments comprising the peptide agents and nucleoside analogue reverse transcriptase inhibitors, nucleotide analogue reverse transcriptase inhibitors, non-nucleoside reverse transcriptase inhibitors, and protease inhibitors can be formulated to contain other ingredients to aid in delivery, retention, or stability of ALGPG-NH$_2$ (SEQ. ID. NO.: 1).

The effective dose and method of administration of a particular peptide agent formulation can vary based on the individual patient and the stage of the disease, as well as other factors known to those of skill in the art. Therapeutic efficacy and toxicity of such compounds can be determined by standard pharmaceutical procedures in cell cultures or experimental animals, e.g., ED$_{50}$ and LD$_{50}$ (the dose lethal to 50% of the population). The dose ratio of toxic to therapeutic effects is the therapeutic index, and it can be expressed as the ratio, LD$_{50}$/ED$_{50}$. Pharmaceutical compositions that exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors that may be taken into account include the severity of the disease state, age, weight and gender of the patient; diet, time and frequency of administration, drug combination(s), reaction sensitivities, and tolerance/response to therapy. Short acting pharmaceutical compositions are administered daily whereas long acting pharmaceutical compositions are administered every 2, 3 to 4 days, every week, or once every two weeks. Depending on half-life and clearance rate of the particular formulation, the pharmaceutical compositions of the invention are administered once, twice, three, four, five, six, seven, eight, nine, ten or more times per day.

Normal dosage amounts may vary from approximately 1 to 100,000 micrograms, up to a total dose of about 10 grams, depending upon the route of administration. Desirable dosages include 250 μg, 500 μg, 1 mg, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 1 g, 1.1 g, 1.2 g, 1.3 g, 1.4 g, 1.5 g, 1.6 g, 1.7 g, 1.8 g, 1.9 g, 2 g, 3 g, 4 g, 5, 6 g, 7 g, 8 g, 9 g, and 10 g. Additionally, the concentrations of the peptide agents can be quite high in embodiments that administer the agents in a topical form. Molar concentrations of peptide agents can be used with some embodiments. Desirable concentrations for topical administration and/or for coating medical equipment range from 100:M to 800 mM. Preferable concentrations for these embodiments range from 500:M to 500 mM. For example, preferred concentrations for use in topical applications and/or for coating medical equipment include 500 μM, 550 μM, 600 μM, 650 μM, 700 μM, 750:μM, 800 μM, 850 μM, 900 μM, 1 mM, 5 mM, 10 mM, 15 mM, 20 mM, 25 mM, 30 mM, 35 mM, 40 mM, 45 mM, 50 mM, 60 mM, 70 mM, 80 mM, 90 mM, 100 mM, 120 mM, 130 mM, 140 mM, 150 mM, 160 mM, 170 mM, 180 mM, 190 mM, 200 mM, 300 mM, 325 mM, 350 mM, 375 mM, 400 mM, 425 mM, 450 mM, 475 mM, and 500 mM. Guidance as to particular dosages and methods of delivery is provided in the literature and below. (See e.g., U.S. Pat. Nos. 4,657,760; 5,206,344; and 5,225,212, herein expressly incorporated by reference in their entireties).

More specifically, the dosage of the peptide agents described herein is one that provides sufficient peptide agent to attain a desirable effect including binding of a capsomere protein, such as p24, and/or interference with capsid assembly and/or inhibition of viral infection, such as HIV and SIV infection. Accordingly, the dose of peptide agent preferably produces a tissue or blood concentration or both from approximately 0.1:M to 500 mM. Desirable doses produce a tissue or blood concentration or both of about 1 to 800 μM. Preferable doses produce a tissue or blood concentration of greater than about 10 μM to about 500:M. Preferable doses are, for example, the amount of peptide agent required to achieve a tissue or blood concentration or both of 10 μM, 15 μM, 20 μM, 25 μM, 30 μM, 35 μM, 40 μM, 45 μM, 50 μM, 55 μM, 60 μM, 65 μM, 70 μM, 75 μM, 80 μM, 85 μM, 90 μM, 95 μM, 100 μM, 110 μM, 120 μM, 130 μM, 140 μM, 145 μM, 150 μM, 160 μM, 170 μM, 180 μM, 190 μM, 200 μM, 220 μM, 240 μM, 250 μM, 260 μM, 280 μM, 300 μM, 320 μM, 340 μM, 360 μM, 380 μM, 400 μM, 420 μM, 440 μM, 460 μM, 480 μM, and 500 μM. Although doses that produce a tissue concentration of greater than 800 μM are not preferred, they can be used with some embodiments. A constant infusion of the peptide agent can also be provided so as to maintain a stable concentration in the tissues as measured by blood levels.

Routes of administration of the peptide agents include, but are not limited to, topical, transdermal, parenteral, gastrointestinal, transbronchial, and transalveolar. Topical administration is accomplished via a topically applied cream, gel, rinse, etc. containing a peptide. Transdermal administration is accomplished by application of a cream, rinse, gel, etc. capable of allowing the peptide agent to penetrate the skin and enter the blood stream. Parenteral routes of administration include, but are not limited to, electrical or direct injection such as direct injection into a central venous line, intravenous, intramuscular, intraperitoneal or subcutaneous injection. Gastrointestinal routes of administration include, but are not limited to, ingestion and rectal. Transbronchial and transalveolar routes of administration include, but are not limited to, inhalation, either via the mouth or intranasally.

Compositions of peptide agent-containing compounds suitable for topical application include, but are not limited to, physiologically acceptable implants, ointments, creams, rinses, and gels. Any liquid, gel, or solid pharmaceutically acceptable base in which the peptides are at least minimally soluble is suitable for topical use in the present invention. Compositions for topical application are particularly useful during sexual intercourse to prevent transmission of HIV. Suitable compositions for such use include, but are not limited to, vaginal or anal suppositories, creams, and douches.

Compositions of the peptide agents suitable for transdermal administration include, but are not limited to, pharmaceutically acceptable suspensions, oils, creams, and ointments applied directly to the skin or incorporated into a protective carrier such as a transdermal device ("transdermal patch"). Examples of suitable creams, ointments, etc. can be found, for instance, in the Physician's Desk Reference and are well known in the art. Examples of suitable transdermal devices are described, for instance, in U.S. Pat. No. 4,818, 540, issued Apr. 4, 1989 to Chinen, et al., hereby incorporated by reference in its entirety.

Compositions of the peptide agents suitable for parenteral administration include, but are not limited to, pharmaceutically acceptable sterile isotonic solutions. Such solutions include, but are not limited to, saline and phosphate buffered saline for injection into a central venous line, intravenous, intramuscular, intraperitoneal, or subcutaneous injection of the peptide agents.

Compositions of the peptide agents suitable for transbronchial and transalveolar administration include, but are not limited to, various types of aerosols for inhalation. For instance, pentamidine is administered intranasally via aerosol to AIDS patients to prevent pneumonia caused by *pneumocystis carinii*. Devices suitable for transbronchial and transalveolar administration of the peptides, including but not limited to atomizers and vaporizers, are also included within the scope of the present invention. Many forms of currently available atomizers and vaporizers can be readily adapted to deliver peptide agents.

Compositions of the peptide agents suitable for gastrointestinal administration include, but not limited to, pharmaceutically acceptable powders, pills or liquids for ingestion and suppositories for rectal administration. Due to the most common routes of HIV infection and the ease of use, gastrointestinal administration, particularly oral, is the preferred embodiment of the present invention.

The peptide agents are also suitable for use in situations where prevention of HIV infection is important. For instances, medical personnel are constantly exposed to patients who may be HIV positive and whose secretions and body fluids contain the HIV virus. Further, the peptide agents can be formulated into antiviral compositions for use during sexual intercourse so as to prevent transmission of HIV. Such compositions are known in the art and also described in the international application published under the PCT publication number WO90/04390 on May 3, 1990 to Modak et al., which is incorporated herein by reference in its entirety.

Embodiments of the invention also include a coating for medical equipment such as gloves, sheets, and work surfaces that protects against viral transmission. Alternatively, the peptide agents can be impregnated into a polymeric medical device. Particularly preferred are coatings for medical gloves and condoms. Coatings suitable for use in medical devices can be provided by a powder containing the peptides or by polymeric coating into which the peptide agents are suspended. Suitable polymeric materials for coatings or devices are those that are physiologically acceptable and through which a therapeutically effective amount of the peptide agent can diffuse. Suitable polymers include, but are not limited to, polyurethane, polymethacrylate, polyamide, polyester, polyethylene, polypropylene, polystyrene, polytetrafluoroethylene, polyvinyl-chloride, cellulose acetate, silicone elastomers, collagen, silk, etc. Such coatings are described, for instance, in U.S. Pat. No. 4,612,337, issued Sep. 16, 1986 to Fox et al., which is incorporated herein by reference in its entirety. Accordingly, methods of making a medicament that inhibits viral replication, specifically, HIV, involve providing a peptide amide comprising, consisting of, or consisting essentially of ALGPG-$NH_2$ (SEQ. ID. NO.: 1) and formulating said medicament for delivery to a subject, including a human, as described above.

Although the peptide agents described herein can be used as research tools to analyze the interaction of the peptide amide with a protein, desirably they are used to inhibit viral replication and/or infection, preferably, HIV replication and infection in a subject. By one method, for example, a subject at risk of becoming infected by HIV or who is already infected with HIV is identified and said subject is provided a peptide amide comprising, consisting of, or consisting essentially of ALGPG-$NH_2$ (SEQ. ID. NO.: 1).

The methods above can be supplemented with administration of an antiviral treatment selected from the group consisting of nucleoside analogue reverse transcriptase inhibitors, nucleotide analogue reverse transcriptase inhibitors, non-nucleoside reverse transcriptase inhibitors, and protease inhibitors. Further, the ALGPG-$NH_2$ (SEQ. ID. NO.: 1) used in these methods can be joined to a support or can be administered in a pharmaceutical comprising a pharmaceutically acceptable carrier.

While the present invention has been described in some detail for purposes of clarity and understanding, one skilled in the art will appreciate that various changes in form and detail can be made without departing from the true scope of the invention. All figures and tables, as well as patents, applications, and publications referred to above are hereby expressly incorporated by reference in their entireties.

What is claimed is:

1. A method of inhibiting the replication of HIV comprising administering a therapeutically effective amount of a peptide comprising the formula ALGPG-$NH_2$ (SEQ. ID. NO.: 1).

2. The method of claim 1, further comprising administering an antiviral agent selected from the group consisting of a nucleoside analogue reverse transcriptase inhibitor, a nucleotide analogue reverse transcriptase inhibitor, a non-nucleoside reverse transcriptase inhibitor, and a protease inhibitor.

3. A method of inhibiting the replication of HIV comprising administering a therapeutically effective amount of a peptide consisting of the formula ALGPG-NH$_2$ (SEQ. ID. NO.: 1).

4. The method of claim 3, further comprising administering an antiviral agent selected from the group consisting of a nucleoside analogue reverse transcriptase inhibitor, a nucleotide analogue reverse transcriptase inhibitor, a non-nucleoside reverse transcriptase inhibitor, and a protease inhibitor.

5. A method of inhibiting the replication of HIV comprising:
    identifying a subject in need of an agent that inhibits the replication of HIV; and
    administering to said subject a therapeutically effective amount of a peptide comprising the formula ALGPG-NH$_2$ (SEQ. ID. NO.: 1).

6. The method of claim 5, further comprising administering an antiviral agent selected from the group consisting of a nucleoside analogue reverse transcriptase inhibitor, a nucleotide analogue reverse transcriptase inhibitor, a non-nucleoside reverse transcriptase inhibitor, and a protease inhibitor.

7. A method of inhibiting the replication of HIV comprising:
    identifying a subject in need of an agent that inhibits the replication of HIV; and
    administering to said subject a therapeutically effective amount of a peptide consisting of the formula ALGPG-NH$_2$ (SEQ. ID. NO.: 1).

8. The method of claim 7, further comprising administering an antiviral agent selected from the group consisting of a nucleoside analogue reverse transcriptase inhibitor, a nucleotide analogue reverse transcriptase inhibitor, a non-nucleoside reverse transcriptase inhibitor, and a protease inhibitor.

* * * * *

SEQUENCE LISTING

```
<160> NUMBER OF SEQ ID NOS: 1

<210> SEQ ID NO 1
<211> LENGTH: 5
<212> TYPE: PRT
<213> ORGANISM: Artificial Sequence
<220> FEATURE:
<223> OTHER INFORMATION: Anti-viral Agent
<220> FEATURE:
<221> NAME/KEY: VARIANT
<222> LOCATION: (5)...(5)
<223> OTHER INFORMATION: Glycine amide, wherein amino group is
      substituted for hydroxyl residue at the terminal carboxyl group

<400> SEQUENCE: 1

Ala Leu Gly Pro Xaa
 1              5
```